United States Patent [19]

Marshall et al.

[11] Patent Number: 4,927,685

[45] Date of Patent: May 22, 1990

[54] TRANSVERSE WEBBER AND STRATIFIED WEBS FORMED THEREWITH

[75] Inventors: Gerald M. Marshall, Somerville; Raymond Hull, Jr., Hampton; Allan P. Farrington, Englishtown, all of N.J.

[73] Assignee: Chicopee, New Brunswick, N.J.

[21] Appl. No.: 99,875

[22] Filed: Sep. 22, 1987

[51] Int. Cl.⁵ .................. B32B 5/08; B32B 5/12; B32B 5/26; D04H 1/70

[52] U.S. Cl. .................. 428/74; 264/113; 264/518; 425/82.1; 428/190; 428/284; 428/286; 428/298; 428/913; 604/365; 604/374; 604/376; 604/378; 604/385.6

[58] Field of Search ............. 428/74, 190, 284, 286, 428/298, 913

[56] References Cited

U.S. PATENT DOCUMENTS

4,701,294 10/1987 Radwanski et al. ............. 264/518
4,767,586 8/1988 Radwanski et al. ............. 264/113

Primary Examiner—James C. Cannon
Attorney, Agent, or Firm—Joseph F. Shirtz

[57] ABSTRACT

A nonwoven web is formed by feeding separate supplies of fibrous material into contact with two separate lickerins that are parallel to each other and rotated toward each other. The fibers from the two lickerins pass through a mixing zone and are accumulated on a moving conveying screen that is moved parallel to the axes of the lickerins. A baffle plate may be inserted into the mixing zone and acts to control the lateral or cross-sectional composition of a web formed by the fibers accumulated on the screen. When different fibrous materials are fed to the lickerin along their length, the vertical composition of the web is altered.

10 Claims, 4 Drawing Sheets

TRANSVERSE WEBBER AND STRATIFIED WEBS FORMED THEREWITH

TECHNICAL FIELD

This invention relates to an improved method and apparatus for forming nonwoven structures consisting of a more or less uniform intermixture of randomly oriented fibers obtained from separate supplies of individualized fibers, such as textile and papermaking fibers.

BACKGROUND OF THE INVENTION

Nonwoven fiber structures frequently consist of a random yet homogeneous agglomeration of long and short fibers. Long fibers are fibers of both natural and synthetic origin that are suitable for textiles. They are longer than 0.25 inches and generally range between 0.5 and 2.5 inches in length. Short fibers are suitable for papermaking and are generally less than about 0.25 inches long, such as wood pulp fibers or cotton linters. It is known in the art that strong nonwoven structures can be made by rapidly and reliably blending inexpensive short fibers with strong long fibers.

Random distribution of the blended fibers results in an isotropic web or structure that is uniformly strong in all directions. The fibers can also be directionally disposed or aligned, resulting in an anisotropic fabric that is strong in the direction of alignment. Nonwoven fabrics are less costly than woven or knitted material, yet are more or less comparable in physical properties, appearance, and weight. Thus, inexpensive nonwoven fabrics are available for a wide variety of products, including, hand towels, table napkins, sanitary napkins, hospital clothing, draperies, cosmetic pads, etc. These nonwoven webs can be particularly advantageous when formed as a layered or composite structure having selective absorbent properties.

The desired utility and characteristics of the nonwoven end product dictate the types of fibers and the relative proportions of long and short fibers in a web. The desired characteristics may include, for example, tear resistance, abrasion resistance, stretchability, strength, absorption or non-absorption to different liquids, heat sealability, and resistance to delamination. Thus, a strong yet absorbent web may advantageously be formed from two or more long and short fibers, such as rayon and wood pulp combined in varying percentages.

There are many different methods and devices useful for making nonwoven webs and other fibrous structures. Conventional carding or garnetting methods produce nonwoven fiber webs, but these are generally limited to textile length fibers.

The "Rando-Webber" process may be used to make nonwoven webs. In this process, pre-opened textile fiber material is delivered to a lickerin that opens the fibers further, and introduces them to a high-velocity low-pressure air stream. The fibers are randomly deposited on a condensing screen to form an isotropic web. While a uniform web of textile fibers can be obtained, this process is not suitable for use with short fibers or blends of long and short fibers.

U.S. Pat. No. 3,512,218 of Langdon describes two lickerins and rotary feed condenser assemblies arranged in parallel one after the other. Isotropic nonwoven webs are formed with this apparatus by feeding fibrous material to the lickerins, where the fibers are individualized and deposited on a condenser screen. A single airstream is divided into two parts and acts to doff the fibers from the lickerins and deposit them onto the screen, where the web is formed. This method cannot be used to homogeneously blend two streams of fibers.

In U.S. Pat. No. 3,535,187 of Woods there is described apparatus for producing a layered web of randomly oriented fibers joined at the interface of adjacent layers by a small zone of textile length fibers extending across the interface. Wood's device provides individualized fibers which are deposited on a pair of cylindrical condenser screens by a pair of respective lickerins acting in cooperation with high speed, turbulent air streams that move faster than the lickerin in order to doff the fibers. However, the air speed must also be controlled so that the fibers do not forcibly impact on the condensers. The condenser screens are positioned closely adjacent to one another and the layers of fibers on the condensers are compressed between the condensers to form a composite nonwoven web with some blending at the interface between layers. However, there is no substantial fiber mixing zone adjacent to the condensers, and the intermixing of fibers is minimal.

One way of making a nonwoven web consisting of a mixture of randomly oriented long and short fibers uses a milling device to individualize short fibers and a lickerin to individualize long fibers. The fibers are mixed in a mixing zone, and the mixture is deposited on a condenser to form a nonwoven web. Though randomly oriented, the mixed fibers are stratified rather than homogeneously blended. The long fibers predominate on one side of the web and the short fibers predominate on the other. In addition, undesirable clumps of fibers or "salt" occur in this web product, because the mill does not completely individualize the short wood pulp fibers.

Another method used to make webs of mixed and randomly oriented long and short fibers introduces pre-opened long and short fibers to a single lickerin for individualization. However, the optimum lickerin speeds for long and short fibers are different. To prevent the degradation of long fibers, this device must operate at the slower speed that is optimum for long fibers. As a result, the speed and throughput of the device is compromised.

Methods and devices which produce a blend of long and short fibers without clumps or salt are disclosed in U.S. Pat. No. 3,772,739 of Lovgren. Lovgren provides for the separate and simultaneous individualization of each type of fiber on separate lickerins, each operating at an optimum speed for the fiber it opens. For example, long fibers such as rayon are supplied to a lickerin operating in the neighborhood of 2400 rpm. Pulpboard is supplied to a lickerin operating in the neighborhood of 6000 rpm, a speed that would damage long fibers. The fibers are doffed from their respective lickerins by separate air streams and are entrained in the separate air streams. These streams are subsequently mixed in a mixing zone in order to blend the fibers. The homogeneous blend is then deposited in a random fashion on a condenser disposed in proximity to the mixing zone. While the Lovgren apparatus is useful, it does not lend itself to the preparation of a wide variety of webs.

Another method of producing homogeneous blends of fibers is disclosed in commonly owned U.S. Pat. No. 3,740,797 of Farrington. Farrington discloses a method and machine wherein supplies of fibers are fed to oppositely rotating parallel lickerins, which are operated at respective optimum speeds to produce individualized long and short fibers. The individualized fibers are doffed from the lickerins by centrifugal force and by high velocity air streams directed against any fibers tending to cling to the lickerin structure. The individualized fibers from each supply are entrained in their respective air streams and are impelled toward each other at high velocities along trajectories that intersect in a mixing zone, where at least a portion of the fibers from each supply may be blended. A condensing means or screen with a vacuum chamber below it communicates with the mixing zone so that the blended fibers are deposited on the condenser screen within a condensing zone to produce an isotropic web of fibers. This screen is moved in a direction, i.e. the "machine direction," which is perpendicular to the axis of the lickerins. In addition, a baffle can be interposed between the air streams to control the degree of mixing and the respective location of the long and short fibers in the composite web.

Farrington provides a method and apparatus for producing an air laid nonwoven web of homogeneously blended and randomly oriented short and long fibers that is isotropically strong and is free of salt. While Farrington provides for a wide variety of nonwoven web products, that process is still insufficient to produce many desirable nonwoven structures or webs.

Thus it would be advantageous to provide a method and apparatus for making thicker webs more rapidly than with the Farrington process, and webs having a wider range of shapes and composite structures than can be made on known machines by known methods.

SUMMARY OF THE INVENTION

The present invention is directed to the high-speed production of blends of long and short fibers that result in a wide variety of composite nonwoven web structures of different widths, thickness, shapes and compositions.

In an illustrative embodiment of the invention two independent fiber sources driven by feed rolls are individualized by parallel counter-rotating lickerins. The individualized fibers are doffed from the lickerins by air streams and centrifugal force, and are carried to a mixing zone. The fibers may be randomly and uniformly mixed in that zone, or may be segregated by type, and then directed to a condensing zone where they are deposited onto a narrow condensing screen which is located in the condensing zone. The mixing zone is below the parallel lickerins and is defined generally by the space between the lickerins and the condensing zone, which is below the mixing zone. The screen is moved parallel to the axes of the lickerins, which is transverse to the conventional orientation. The motion of the screen with respect to the lickerins and the frame which houses them defines an input or rear end of the condensing zone, where the screen first enters the condensing zone and receives individualized fibers, and an exit or front end, where the formed web ceases to receive fibers and is expelled from communication with the condensing zone. At any given moment during operation of the apparatus, the web is formed in the condensing zone between the input and exit ends, which also generally define the operating length of the lickerins.

Duct plates are used to additionally define a path between the lickerins and the condenser screen, and a vacuum chamber with a slot located below the screen is preferably used to form the air streams that doff the fibers from the lickerins and help deposit the fibers onto the screen. Since the screen travels parallel to and between the lickerins axes, there is a high-speed transverse formation of a web of nonwoven fibers. The transverse webber according to the invention provides a formation zone whose length is limited only by the practical length of the lickerins and whose width is limited only by the practical duct configuration between the lickerins and the screen.

Composite and layered structures can be made by varying the material introduced to the lickerins along the length of each lickerin. Webs having different cross-sectional shapes can be generated by varying the configuration of the duct plates or the vacuum slot in the condensing zone, by introducing baffles in to the mixing zone, or by programmably driving the feed rolls, or combinations thereof.

According to the invention, separate sources of short and long fibers, such as pulp and rayon, respectively, are individualized by separate lickerins and formed into a web. Each fiber source is guided by feed rolls and a nose bar into engagement with its lickerin, and each lickerin is rotated at a high speed that is suitable for the fibers it is acting on. The two lickerins are parallel to each other and rotate toward each other, i.e. in opposite directions. The nose bar and lickerin are arranged to provide a fiberizing station having the optimum opening relationship for the fibers. Each lickerin acts on its fiber supply and rapidly individualizes the fibers through violent contact between the fiber supply and the rapidly rotating teeth of the lickerin.

The counter-rotating lickerins create a centrifugal force that tends to tangentially throw the individual fibers from each lickerin toward the fibers from the other lickerin. Gravity, an air stream naturally generated by the rotation of each lickerin, and the high speed air stream created by a suction force below the condenser screen tend to impel the tangentially thrown fibers from the lickerin downward and toward each other. These tangential and downward vector components carry the individualized fibers to a centrally disposed mixing zone between but below, the lickerins.

The streams of individual fibers entering the mixing zone from the two lickerins are dilute, allowing the two streams to intersect each other, such that the fibers cross each other without a substantial number of collisions. As a result, the fibers from the lickerin to the left of the condenser screen tend to reach predominately the right side of the screen and visa versa.

A different mixing pattern of the fibers can be accomplished by inserting a baffle into the mixing zone between the lickerins. This baffle intersects part of each stream of fibers and deflects it back in the opposite direction, such that the long and short fibers are spread across the lateral width of the web. This results in a proportionally uniform mixing of the long and short fibers across the web. If the baffle completely intersects the streams, the material from the lickerin on the left is reflected back to the left and vise versa, so that a product with a distribution essentially opposite that with no baffle is created. Therefore, the present invention produces products which may have different compositions than in the prior art, for example, webs formed in laterally separated strips.

The deposition of fibers occurs as the condenser screen moves along the length of the lickerins, e.g. 40 inches. Thus for the same screen speed and feed rate the material deposited per inch of screen width is greater than in the prior art wherein the lickerin axes are perpendicular to the screen movement direction and the condensing zone is only the separation between the ducts extending from the lickerins, i.e. about 4 inches.

The width of the web is determined, according to the invention, by the distance between the lickerins, if parallel ducts are used. However, the ducts may diverge from the lickerins to the condensing zone. In such a case the width is determined by the angle of divergence and the distance from the lickerins to the screen, which are in turn limited by the ability of the fiber/air stream to expand while maintaining a uniform flow profile without separation from the duct walls. When the condenser screen is in the form of an endless moving belt, the length of the web is generally continuous, unless and until the supply of fiber is exhausted. The thickness and density of the web is determined primarily by the fibers chosen, the proportion at which they are mixed, the feed roller speed, and the rate at which the condensing screen is moved.

Different composition pulp and textile fibers can be fed simultaneously to the respective lickerins in a side-byside relationship. In one such embodiment, pulp and textile fibers are fed into the device toward the input end of the condensing zone to form a bottom layer of the web, while two other materials are fed toward the exit end to form a top layer. In this way, different regions of the mixing zone can be defined, and the resulting web can be formed as horizontal and vertical layers or web zones. Each web zone is integrally associated with its adjacent web zone or zones by entanglement of the fibers across the interface; and each zone has a different but uniform composition of randomly oriented fibers.

BRIEF DESCRIPTION OF THE DRAWINGS

The foregoing advantages and numerous other features of the invention will be more readily understood and appreciated in light of the following detailed description and accompanying drawings, wherein.

DESCRIPTION OF ILLUSTRATIVE EMBODIMENTS

Figure 1:
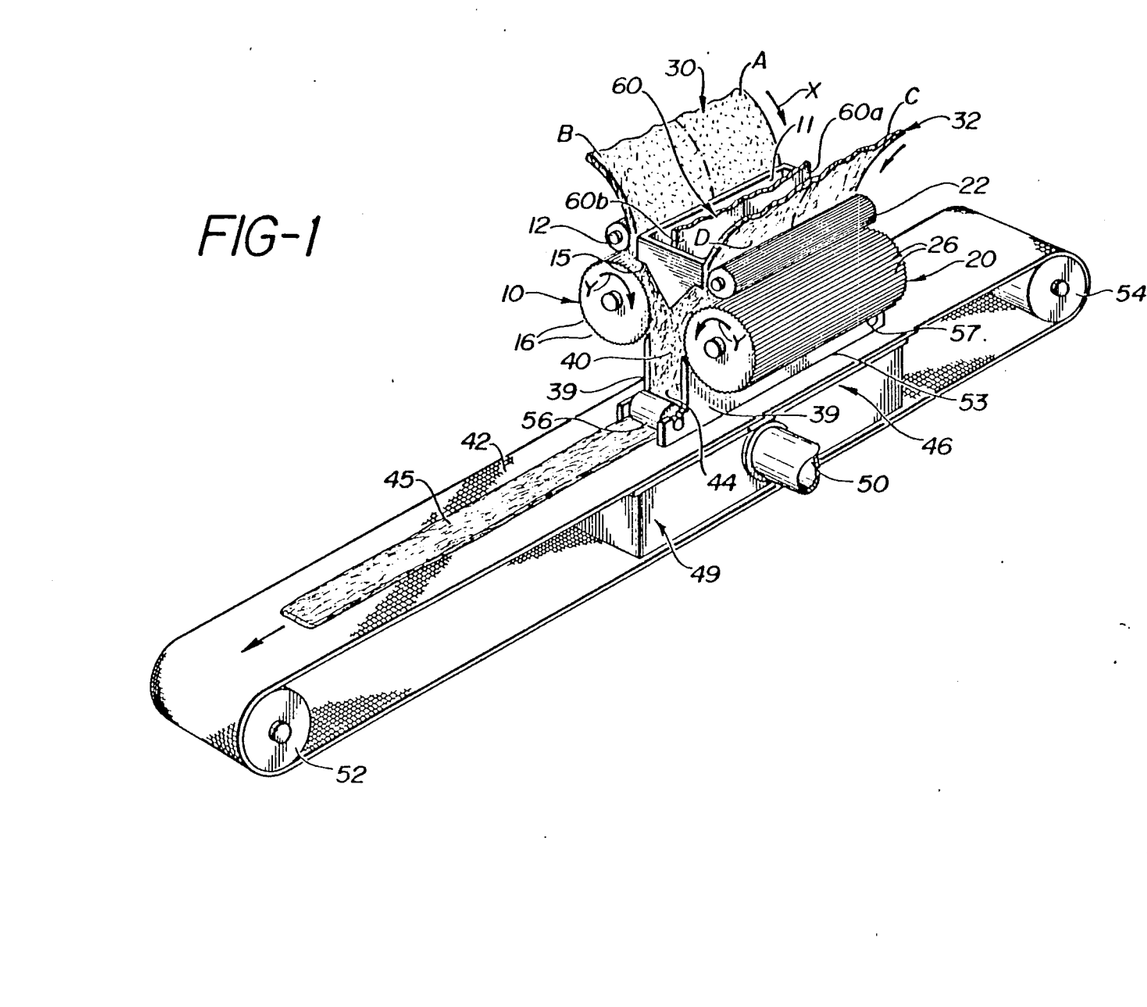
FIG. 1 is a schematic view of a transverse webber according to the invention, showing the main components thereof.
Figure 2:
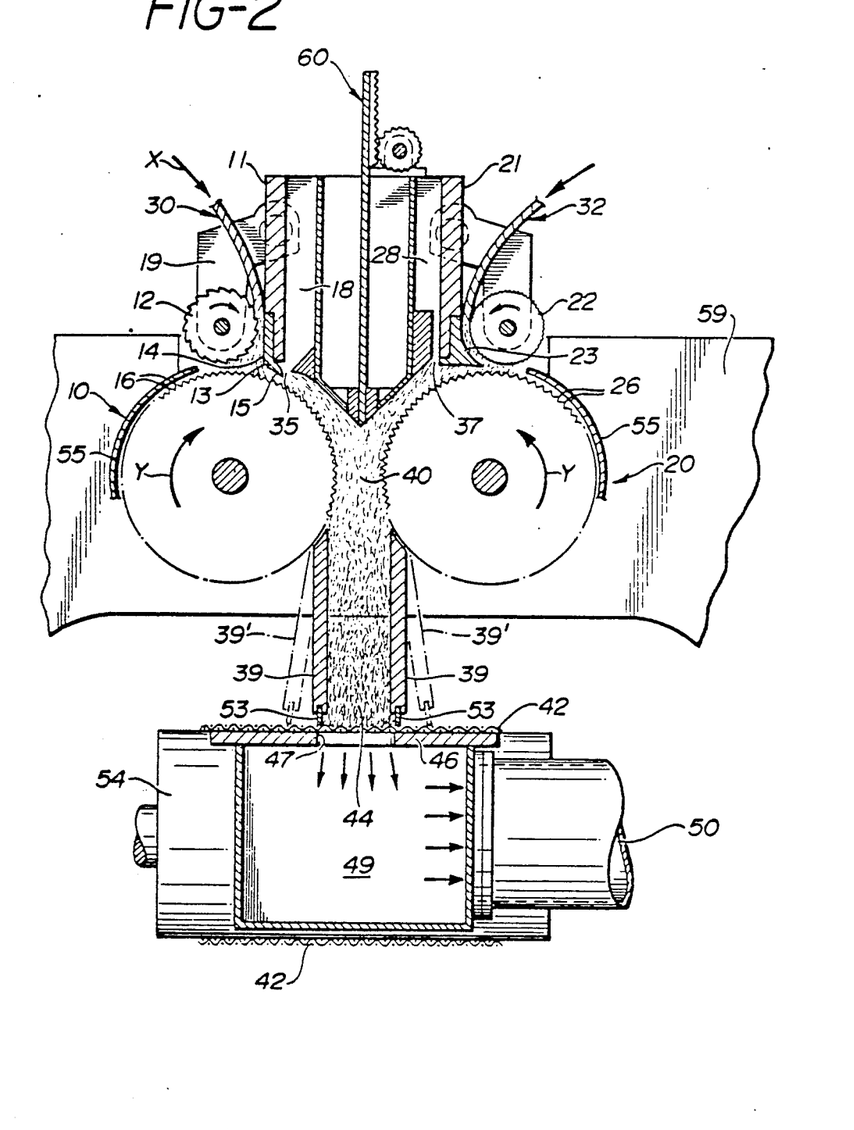
FIG. 2 is a more detailed cross-sectional view of an apparatus according to the invention.

FIGS. 1 and 2 show perspective schematic and crosssectional views of the main components of an apparatus according to the invention. The invention is adapted to combine short and long fibers into a nonwoven web having variable horizontal and vertical cross-sectional compositions. Principally the apparatus comprises two lickerins 10, 20 operating in parallel. One lickerin 10 is adapted to individualize short fibers and the other lickerin 20 individualizes long fibers. The individualization of the fibers, but not the formation of the web, is generally performed according to commonly owned U.S. Pat. No. 3,740,797 to Farrington, the details of which are incorporated herein by reference.

Referring first to the short fibers, shown on the left in FIG. 1, wood pulp, in the form of a pulpboard 30, is directed between a plate 11 (FIG. 2) and a wire wound feed roll 12. The plate 11 has a nose bar 13 on its lower part, which provides an anvil for the pulpboard 30 during individualization of the short fibers. The fibers are individualized by the rotating lickerin 10 disposed below the feed roll 12 and operatively adjacent to the nose bar 13. The nose bar 13 assists in directing the pulpboard 30 along a path defined by the plate 11, the feed roll 12, the lickerin 10, the nose bar 13 itself, and an inclined face 15 adjacent to the lickerin 10. These elements form a fiberizing station where the fibrous material, i.e., pulpboard 30, is converted into individual fibers. The inclined face 15 is spaced a short distance from the teeth 16 of the lickerin 10 and the pulpboard 30 is individualized into fibers by the teeth 16 of lickerin 10 acting on pulpboard 30 as it is brought in contact with the teeth 16 by the nose bar 13.

Typical short fibers include wood pulp fibers from various types of wood, cotton linters, asbestos fibers, glass fibers, and the like. Wood pulp fibers are the most frequently used, due to their low cost and ready availability. Pulp fibers are commercially available in the form of pulp boards of varying sizes and thicknesses.

For short fibers, the nose bar 13 may have a relatively flat sidewall 14 (FIG. 2). The feed roll 12 is eccentrically mounted to permit adjustment relative to side wall 14 and nose bar 13, as shown for example in FIG. 2 by bracket 19. The bracket 19 and feed roll 12 are resiliently biased to direct the pulpboard 30 against the nose bar 13 by known means, and to drive the pulpboard into engagement with the teeth 16 of lickerin 10. This design permits the use of pulpboards of varying thicknesses.

Feed roll 12 is supported on a shaft and is rotated by conventional motor means (not shown) at a speed determined by the rate at which the pulpboard 30 is to be fed to the lickerin 10. This rate determines the amount of pulp fibers deposited to form the web in a unit of time. The pulpboard 30 is fed to the feed roll 12 in the direction shown by the arrow X in FIG. 1.

The lickerin 10 is likewise supported on a shaft and is rotated at a predetermined speed by a conventional motor (not shown). Lickerin 10 is adapted to rapidly and reliably fray and comb the pulpboard 30 by engagement with the teeth 16 until individual fibers are liberated from the pulpboard. Speeds in the neighborhood of 6000 rpm have been found suitable for this purpose. The teeth 16 are chosen to have an optimum profile for the chosen short fiber material represented by pulpboard 30.

Long fibers are individualized in much the same manner as the short fibers, as shown on the right side of FIGS. 1 and 2. Typical long fibers include synthetic fibers, such as cellulose acetate, vinyl chloride-vinyl acetate and viscose staple rayon fibers, and natural fibers, such as cotton, wool or silk. Long fibers, such as rayon, are commercially available in bales, with varying fiber lengths.

A source of long fibers is provided, usually in the form of a carded batt 32, as when rayon is used as the fiber source. Batt 32 is introduced to lickerin 20 via a second wire wound feed roll 22 acting in cooperation with a plate 21 (FIG. 2) and a nose bar 23. However, the nose bar 23, adapted for use with long fiber sources, differs from the nose bar 13 used with pulp. Since rayon and other long fiber sources lack the physical integrity of pulpboard, the batt 32 must be more positively restrained and directed into engagement with the lickerin 20. As shown in FIG. 2, the nose bar 23 is curved to essentially conform to the adjacent surface of the second feed roll 22. In this manner, the fibers in the rayon source are maintained in position with respect to the second feed roll 22 until they are delivered to the teeth 26 of lickerin 20. The lickerin 20 is rotated at speeds such that the teeth 26 can comb long fibers from the batt 32 without degrading or damaging the long fibers. Speeds in the neighborhood of 3000 rpm have been found suitable for this purpose.

The teeth 26 of lickerin 20 are generally shorter than the teeth 16 of lickerin 10, and have a smaller pitch. Excellent results can be obtained when the tooth pitch and height of teeth 26 each range between about ⅛–½ inches. The angle of teeth 26 varies between −10 and +20 degrees.

A support structure or frame and drive means are, of course, provided for the various elements of the invention, as shown generally in the figures. Additionally, the nose bars, feed rolls, etc. can be adjusted with respect to each other in order to achieve optimal results.

The long and short fibers may be individualized simultaneously or sequentially, and as shown in FIG. 1 there may be more than one type of each fiber (i.e., short fiber pulpboards A, B and long fiber batts C, D) distributed over portions of each lickerin. The lickerins 10, 20 are rotated toward each other, as shown by the arrows Y in FIGS. 1 and 2. The fiber sources, their distribution, and the speed and relative proportions at which they are individualized, are chosen in order to produce a web having the desired structure and combination of fibers.

The individualized long and short fibers are doffed from the lickerins, and are directed toward each other in a mixing zone 40. From the mixing zone the fibers pass to a condensing zone 44 containing a condenser screen 42. This movement of the fibers is assisted by air streams. As shown in FIG. 2, high velocity air streams which doff the fibers and direct them to condenser screen 42 can be established by a suction force created by a high vacuum chamber 49 located below the screen. This vacuum is formed by a fan driven by a motor (not shown) and drawn through duct 50 (FIG. 2). The vacuum draws air through ducts 35, 37, past the lickerins 10, 20 and the nose bars 13, 23, through the mixing zone 40 and the condensing screen 42, to the chamber 49. Since the fibers travel the same path as the air streams from the lickerins to the mixing zone, the fibers are impelled to move more rapidly and reliably from the lickerins 10, 20 to the condensing screen 42, where they form the web 45. In order to assist in doffing fibers from the lickerins 10, 20, the air streams are directed at the lickerin teeth 16, 26 at a predetermined angle and velocity, causing a uniform flow pattern at and around the teeth. Advantageous manipulation of the air streams is further described in Farrington, U.S. Pat. No. 3,740,797.

The web 45 is formed in the condensing zone 44, which is a space below and proximate to the mixing zone 40, just above the condensing screen 42, and between duct plates 39. The length of the condensing zone 44 corresponds to the length of the lickerins 10, 20. Thus, the condensing zone 44, according to the invention, is in the form of a long trough adapted to receive individualized fibers from above.

The duct walls 39 shown in FIG. 2 are parallel and define the width of the condensing zone 44. However, these walls may be replaced with walls 39' to that diverge (as shown in dotted line) at angles up to 15 or 20 degrees in order to form a web wider than the separation of the lickerins.

The condensing screen 42 preferably comprises an endless conveyor that is guided over conveyor rollers 52, 54 (FIG. 1), such that it may pass about the high vacuum chamber 49. One or both of the rollers 52, 54 are driven so as to move screen 42 at a controlled rate.

When using entraining air streams, the vacuum chamber 49 will communicate with the condensing zone 44 through the mesh screen 42 via a suitable aperture 47 provided in suction plate 46 (FIG. 2). The aperture generally corresponds to the cross section of the space defined by the duct plates 39 and 59. The conveyor screen 42 is positioned to travel below and in communication with the condensing zone 44, and in a direction that is parallel to the axes of rotation of the parallel lickerins 10, 20. As a result, the web 45 is formed as a continuous sliver expelled from the condensing zone 44 at right angles to the direction of the fiber supply input and transversely with respect to the rotating lickerins 10, 20. The web 45 is not condensed, as it is in known devices, in a plane formed beneath the lickerins, having a width corresponding to the length of the lickerins, and moving perpendicular to the axis of rotation of the lickerins.

The thickness of the web according to the present invention is inversely proportional to the speed of the screen 42. The faster the screen 42 withdraws the forming web 45, the thinner the resulting web. However, the structure and orientation of the present condensing zone 44 with respect to the mixing zone 40 permits much thicker, albeit narrower, webs to be formed far more rapidly than by other prior techniques.

The screen 42 may communicate with other conveyors, thereby delivering the web 45 for further processing as desired. Such processing may include bonding, as described for example in Lovgren, U.S. Pat. No. 3,772,739; shape-forming procedures; and final finishing of the web product.

Figure 4:
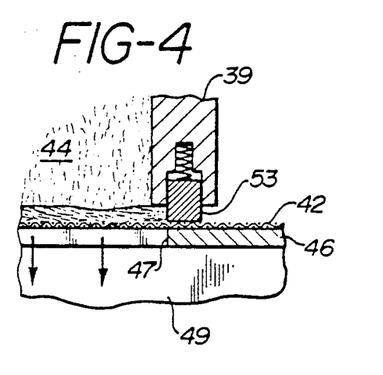
FIG. 4 is a fragmentary view in section showing a portion of the condenser seals.

In order to seal off the lower ends of ducts 39 and to maximize the efficiency of the suction fan, duct plates 39 are extended downward toward the screen 42 and terminate just above the screen 42. The duct plates 39 may additionally be provided with floating seals 53, which are biased into contact with the screen 42 by a spring located behind the floating seals in a recess in plates 39 (FIG. 4). Lickerin covers 55 (FIGS. 2 and 8B) may also extend about the outer periphery of the lickerins and engage plates 39 to provide an additional seal for the vacuum which forms the air streams.

Figure 3:
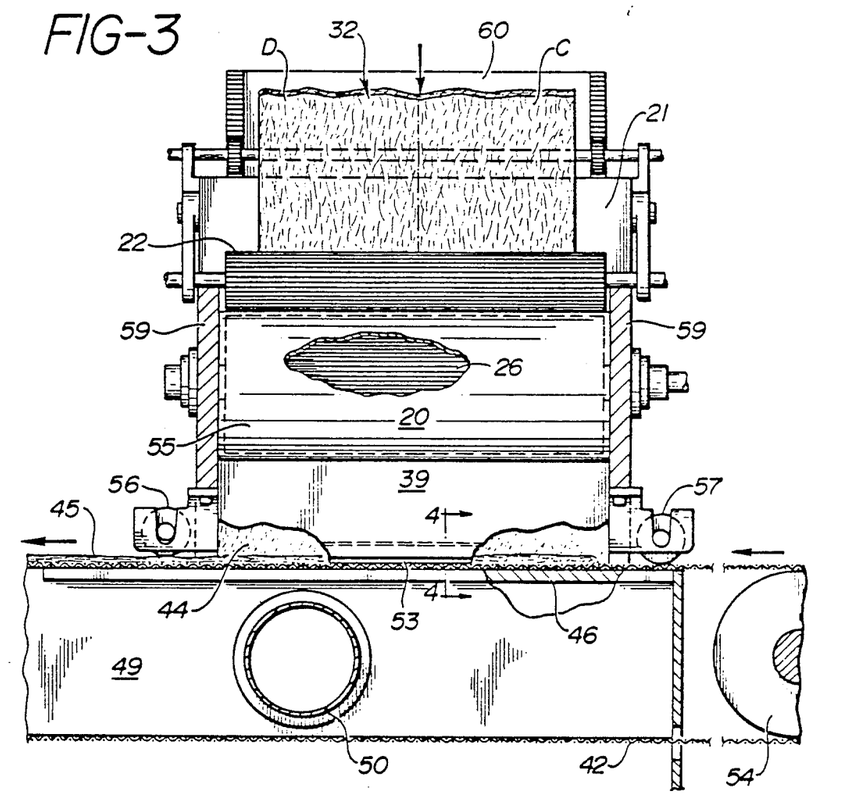
FIG. 3 is a side view of the apparatus of FIG. 2.

At the places where the screen 42 enters and leaves the condensing zone 44, rolling seals 57, 56, respectively, are provided on duct plates 59 (FIG. 3). The sealing rolls 56, 57 are disposed between the parallel edges of duct plates 39 and are free to rotate on the screen and web to accommodate movement of the screen and web. When the web 45 exits the condensing zone 44 supported by the screen 42, it passes beneath sealing roll 56. Besides maintaining the vacuum, the duct plates 39 serve to guide the fibers to the condensing zone 44 and together with the duct plates 59, the floating seals 53, and sealing rolls 56, 57, they improve the efficiency of the suction air flow.

Figure 5:
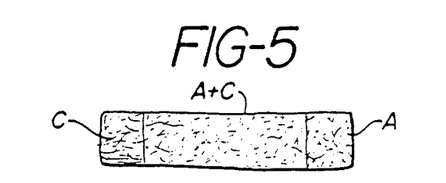
FIGS. 5-7 illustrate cross sections of exemplary composite nonwoven web structures.
Figure 6:
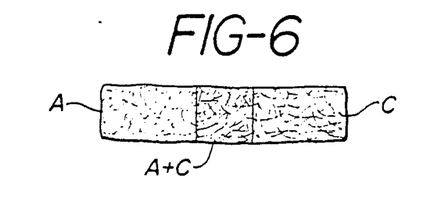
Figure 7:
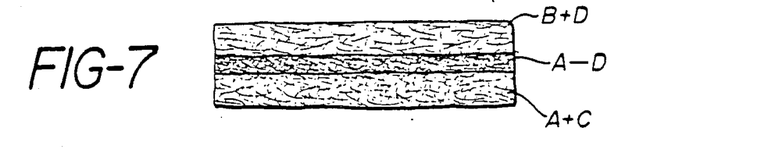

The device according to the invention is provided with a retractable baffle 60 disposed within a plane passing perpendicularly between the lickerins 10, 20 and transecting the mixing zone 40. Although the baffle can be placed so that its downward leading edge falls at any predetermined point at or above the moving condenser screen 42, three distinct qualitative positions can be defined. When the baffle 60 is in the up or fully retracted position, its leading edge is removed from any functional contact with the fiber streams leaving the lickerins. When the baffle 60 is fully down, its downward leading edge is at or above the screen 42 at a predetermined position within the mixing zone 40 where it completely intercepts the fiber streams. Finally, the baffle 60 can be positioned so that its downward leading edge corresponds to a predetermined blend point within the mixing zone 40 where it partially blocks the fiber streams. A wide variety of composite structures can be generated by varying the position of the baffle 60 and by feeding one or more materials via each of the feed rolls 12, 22. FIGS. 5-7 illustrate exemplary composite nonwoven web structures as described according to the following examples. It will be understood by skilled practitioners that these examples represent only a few of the many structures that can be made. Moreover, it will be evident from the examples that, because of the transverse discharge of the web 45, a uniformly blended web is formed which is unobtainable in the same manner in known devices, such as the Farrington method and apparatus. On the contrary, the transverse webber tends to deposit the fibers into a web according to unique zone-forming patterns. These patterns can be manipulated to produce new and useful composite structures.

EXAMPLE 1

The same fiberizating stations (i.e. lickerin, nose bar and feed roller) are set up at each side of the screen. Then identical short fiber pulpboards 30 or long fiber batts 32 are supplied to both of the lickerins 10, 20, via the feed rolls 12, 22. The resulting web 45 is a homogeneous nonwoven web consisting of one kind of fiber. The result is the same for any position of the baffle 60.

EXAMPLE 2

Two different fiber materials 30, 32 in the form of short and long fibers A, C respectively, are delivered to the feed rolls 12, 22 respectively, with each different fiber source being coextensive with one of the lickerins 10, 20. When the baffle 60 is in the up position, a composite web is formed having three lateral zones, each running in the machine direction. A schematic cross-sectional view of this product is shown in FIG. 5.

The zone-like composite structure is a consequence of the trajectories of the fibers doffed from the lickerins, passed through the mixing zone 40 and then formed into a transverse web within the condensing zone 44. In a conventional webber, any such nascent zones tend to be cancelled or unified by continuous withdrawal of the forming web in the standard longitudinal machine direction, i.e. the direction in which such zones would form. However, by withdrawing the forming web in the transverse direction, the zones form as a result of the fiber deposition pattern caused by the fiber trajectories.

When the baffle 60 is up, it does not alter the dilute fiber airstream trajectories as they pass through the mixing zone 40 to the condensing zone 44. The fibers within the air streams retain a component of motion tending to throw them away from their respective lickerin and toward the web on the side of the opposing lickerin. As a result, the fibers tend to pass each other within the mixing zone 40 because the streams are so dilute that there is little tendency for fiber collisions. Thus, the fibers are predominantly deposited toward opposite sides of the condensing zone 44. As shown in FIG. 5, short fibers A originating from a left-hand lickerin tend to form a narrow right-hand fiber zone A containing predominantly fibers A. The long fibers C originating from the right-hand lickerin tend to form a narrow left-hand zone C containing predominantly fibers C. Between the fiber zones A and C is a wider transition zone containing a blend of fibers A+C. At the boundaries of the zones the fibers are entangled so that the web is formed in one piece.

EXAMPLE 3

The fiber sources of Example 2 are used, but the baffle 60 is positioned at a blend point within the mixing zone 40 in order to influence the trajectories of the individualized fibers prior to final deposition as a web on the screen 42. The individualized fibers passing through the mixing zone 40 and on to the condensing zone 44 from each lickerin fall within a range or angle of trajectories, in the manner of a spray exiting a nozzle. The baffle 60, when positioned at the predetermined blend point, intersects at least part of the trajectory angle, causing some of the fibers and any entraining air flow within that part of the angle to bounce off the baffle 60 back toward its own originating side of the condensing zone 44.

If the baffle blend point is chosen so that approximately equal volumes of fiber from each lickerin are redirected by the baffle 60, as are permitted to pass under the baffle 60 without interruption, a uniformly blended web of short and long fibers A+C is obtained. The blend point can, of course, be chosen to provide a wide variety of fiber deposition patterns and resulting nonwoven web structures.

EXAMPLE 4

In yet another embodiment, the baffle 60 is placed in a down position, approximately 2 inches above the screen 42. The two different fiber sources A, C of Example 2 are used such that each fiber is supplied over an operative length of one of the parallel lickerins 10, 20. In this case, substantially all of the fiber trajectories are interrupted by the baffle, tending to throw the fibers back toward their originating side of the condensing zone 44. The result is a web similar to the web in Example 2, but with the fiber zones A and C in reverse order, and a narrower transition zone A+C as shown in FIG. 6.

It should be appreciated that regardless of the position of the baffle, there will be some distribution of both long and short fibers across the web due to the turbulent air flow. Thus the zone representations in FIGS. 5 and 6 merely show the predominate fibers in each. The proportion of fibers in each zone may also be regulated by the rate at which the fiber sources 30, 32 are fed to the lickerins. A fiber fed at a faster rate will produce a greater concentration of that product in the web, although it will be distributed across the web in a manner determined by the baffle position.

Each lickerin 10, 20 need not be supplied entirely with one fiber source, provided that all of the fibers supplied to each lickerin conform to the fiber type (short or long) for which the lickerin is adapted. Thus, for example, four fiber sources A-D can be equally distributed among the two lickerins, each such source covering half of its respective lickerin. FIG. 1 illustrates this embodiment. The pulpboard 30 has a portion with short fibers A and another portion with short fibers B, both of which are fed to lickerin 10. Textile fiber batt 32 also has two portions for producing long fibers C, D which are fed to lickerin 20. The fiber combination A, C toward the input end of the apparatus produces a lower layer of the web while the fiber combination B, D toward the exit end of the apparatus produces an upper layer. Thus, the resulting product has both horizontal or lateral zones and verticallyarranged zones of fiber compositions.

EXAMPLE 5

The multiple fiber supplies A-D of FIG. 1 are fed to the apparatus with the baffle in a blend point position to promote uniform mixing and deposition of fibers. The two rearward fiber sources A and C in the machine direction apply their fibers on a portion of screen 42 first. As this portion of the screen moves toward the exit it passes below the transition between sources AC and BD, and a transition layer having a mixture of all four fibers is laid down on top of the lower layer which is a uniform blend of fibers A and C. As the screen portion moves under the region of the lickerins which is fed fibers B, D, these are deposited as an upper uniformly blended layer B and D. A cross section of this product is shown in FIG. 7.

EXAMPLE 6

Figure 8A:
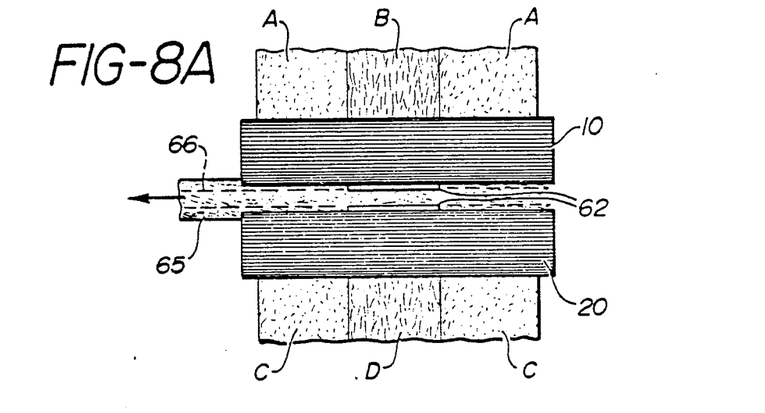
FIGS. 8A and 8B are schematic top and end views of an apparatus according to the present invention with a fixed shield installed in the condensing zone.
Figure 8B:
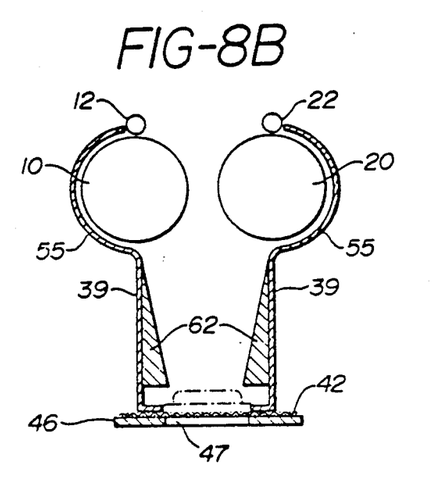
Figure 9A:
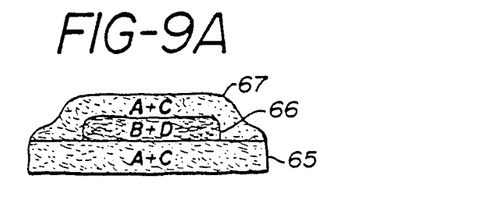
FIGS. 9A and 9B are cross sectional and top views, respectively, of a product made according to the apparatus of FIG. 8.

An alternative product as shown in FIG. 9 may be made by installing fixed shields 62 (FIG. 8A and 8B) in the condensing zone 44 toward the middle of the machine and feeding three separate fiber portions to the lickerin, e.g. A and C, B and D, and A and C. The fixed shields 62 are generally disposed at a horizontal position above the forming web in the middle, where fiber portions B and D are laid down. Thus a first wide layer 65 is deposited which is a mixture of fibers A and C (FIG. 9A). Then a middle layer 66 is added. This layer is narrower and comprises fibers B and D because shields 62 make the condensing zone narrower (FIG. 8B). Finally, a third or top layer 67 is added. Layer 67 may also be a blend of fibers A and C so that the middle layer 66 of fibers B and D is completely surrounded by fibers A and C.

A product in which a middle layer is surrounded by other layers can be very advantageous as a absorber, e.g. a diaper or sanitary napkin. With such a product the inner fiber blends, e.g. B and D, in layer 66 of FIG. 9A, are selected to be high absorbency fibers. For example this layer may be made predominately of pulp or superabsorbing fibers. The outer fibers, e.g. A and C are selected for their wicking property, i.e. the ability to move liquid. For example, Rayon fibers have good wicking capability. With such a product the moisture is directed away from the user's skin and clothing by the wicking fibers and is retained in the center of the product by the high absorbency fibers.

Figure 9B:
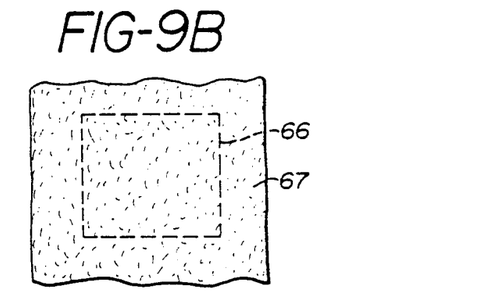

If the feeding of the pulp or high absorbency fibers is intermittent, separate patches of this material will be buried along the web (FIG. 9B). In later processing the web can be separated between these patches to form individual products. For example, these products may be surgical pads with absorbent, inexpensive, but unattractive pulp layers, concealed by a polyester cover layer.

OTHER VARIATIONS

Various other products can be made in segments by starting and stopping the condenser screen and by starting and stopping or sequentially feeding the various fiber materials to the lickerins. Also, fibers may be included which provide properties to the product other than moisture handling. For example a fibrous material with great resiliency may be used to give a product, e.g. a napkin, a springy characteristic that makes it feel like a plush fabric.

As another example, the product shown in FIG. 7 can be formed with the present invention to have a top layer of 70% polyester and 30% synthetic pulp. The middle is a transition region and the bottom layer is 90% pulp and 10% synthetic pulp used as a binder. This is useful as an adult incontinence product in which the upper layer is in contact with the user's skin. One object of this product is to keep the water absorbency pulp away from the user's skin.

A still further product may have an upper layer of 100% polyester, which is nonabsorbent and resilient. The middle layer may be a mixed blend of polyester and pulp, while the bottom layer is pulp and synthetic pulp, which is resilient and absorbent.

While the present invention has been particularly shown and described with reference to preferred embodiments thereof, it will be understood by those skilled in the art that various changes in form and details may be made therein without departing from the spirit and scope of the invention. In particular, when multiple sources are fed to a lickerin they need not each occupy 50% of the space. One may occupy more space than another and there may be gaps between them. Also other products may be created by sequentially feeding the products or halting the feeding for certain periods.

What is claimed is:

1. A nonwoven fiber structure having at least one layer with a preponderance of a first fiber material toward one lateral edge, a predponderance of a second fiber material different from said first fiber material toward the other lateral edge, a first transition zone of fibers in between, further including a second layer over said one layer having a preponderance of a third fiber material toward said one lateral edge, a fourth fiber material different from said third fiber material toward the other lateral edge, a second transition zone of fibers in between said preponderance of third and fourth fibers and a third transition zone between said first and second layers.

2. A nonwoven fiber structure as claimed in claim 1, wherein the two fiber material in said second layer are the same.

3. A nonwoven fiber structure as claimed in claim 1 wherein the structure is a continuous web.

4. A nonwoven fiber structure having at least one layer with a preponderance of a first fiber material toward one lateral edge, a preponderance of a second fiber material different from said first fiber material toward the other lateral edge, a first transition zone of fibers in between said preponderances of said first and said second fiber materials, a second layer narrower than said one layer and over said one layer having a preponderance of a third fiber material toward one lateral edge, a fourth fiber material toward the other lateral edge and a second transition zone of fibers in between said preponderances and a third and fourth fibers, a third layer over the second layer and wider than the second layer, said third layer having a fifth fiber material toward said one lateral edge and a sixth fiber material toward the other lateral edge.

5. A nonwoven fiber structure having at least one layer with a preponderance of a first fiber material toward one lateral edge, a preponderance of a second fiber material toward the other lateral edge and a first transition zone of fibers in between, a second layer narrower than said one layer over said one layer having a predponderance of a third fiber material toward said one lateral edge, a fourth fiber material toward the other lateral edge and a second transition zone of fibers in between, a third layer over the second layer and wider than the second layer, said third layer having a fifth fiber material toward said one lateral edge and a sixth fiber material toward the other lateral edge, wherein the combination of of the first and second fiber materials and the combination of the fifth and sixth fiber materials both have a low fluid absorbency and good wicking capability; and wherein the combination of the third and fourth fiber materials has good fluid absorbency.

6. A nonwoven fiber structure comprising:

a first layer in the form of a uniform blend of first and second different fiber materials;

a second layer overlaying the first layer and being in the form of a uniform blend of third and fourth fiber materials different from one another and different from said first and second fiber materials, said second layer being narrower than the first layer; and a third layer overlying the second layer and being in the form of a uniform blend of fifth and sixth fiber materials, said third layer having approximately the width of the first layer.

7. An integral nonwoven fiber structure having one layer of a first blend of fiber materials and a second layer narrower than said one layer formed of a second blend of material different from said first blend wherein at least one of said first and second blends is a blend of at least two different types of fiber materials and said first and second blends form a transition between said one layer and said second layer which hold both of said layers together as an integral unit.

8. The integral nonwoven fiber structure as claimed in claim 7 wherein the structure is a continuous web.

9. The integral nonwoven fiber structure as claimed in claim 7 wherein said at least one blend is a blend of short fibers and long fibers.

10. The integral nonwoven fiber structure as claimed in claim 7 wherein said at least one blend is a blend of heat sealable and non-heatsealable fibers.

* * * * *

UNITED STATES PATENT AND TRADEMARK OFFICE
CERTIFICATE OF CORRECTION

PATENT NO. : 4,927,685

DATED : May 22, 1990

INVENTOR(S) : Gerald M. Marshall et al.

It is certified that error appears in the above-identified patent and that said Letters Patent is hereby corrected as shown below:

Claim 2, Column 12, Line 57: "material" should be --materials--.

Claim 4, Column 13, Line 4 : "and a third" should be --and third--.

Claim 5, Column 13, Line 24: "of of" should be --of--.

Signed and Sealed this

Sixth Day of October, 1992

Attest:

DOUGLAS B. COMER

Attesting Officer

Acting Commissioner of Patents and Trademarks